(12) United States Patent
DiMatteo

(10) Patent No.: US 6,315,752 B1
(45) Date of Patent: Nov. 13, 2001

(54) IMPLANTABLE BYPASS DEVICE

(75) Inventor: Kristian DiMatteo, Watertown, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/277,649

(22) Filed: Mar. 26, 1999

(51) Int. Cl.[7] .............. A61M 5/00; A61M 5/32; A61N 25/00; A61N 25/16; A61F 2/06
(52) U.S. Cl. ............... 604/8; 604/175; 604/532; 604/535; 623/1.16; 623/1.37
(58) Field of Search ................... 623/1, 1.1, 901, 623/1.13, 1.14, 1.11, 1.15, 1.16, 1.23, 1.27, 1.35, 1.37, 1.49–1.51, 1.54, 11–12; 604/8, 523, 532–535, 538, 284, 264, 174–175; 128/898

(56) References Cited

U.S. PATENT DOCUMENTS

| | | |
|---|---|---|
| 3,683,926 | 8/1972 | Suzuki . |
| 4,878,906 | 11/1989 | Lindemann et al. . |
| 5,304,220 | 4/1994 | Maginot . |
| 5,456,712 | 10/1995 | Maginot . |
| 5,571,167 | 11/1996 | Maginot . |
| 5,575,817 | 11/1996 | Martin . |
| 5,634,941 | 6/1997 | Winston et al. . |
| 5,755,778 | * 5/1998 | Kleshinski ............... 623/1 |
| 5,800,522 | * 9/1998 | Campbell et al. ........ 623/1 |
| 5,879,321 | 3/1999 | Hill . |
| 5,972,017 | 10/1999 | Berg et al. . |
| 5,989,287 | * 11/1999 | Yang et al. . |
| 6,019,788 | * 2/2000 | Butters et al. . |
| 6,026,814 | * 2/2000 | LaFontaine et al. . |
| 6,086,553 | * 7/2000 | Akbik . |
| 6,146,419 | * 11/2000 | Eaton . |

FOREIGN PATENT DOCUMENTS

| | | |
|---|---|---|
| WO 98/06356 | 2/1998 | (WO) . |
| WO 99/51165 | 10/1999 | (WO) . |

* cited by examiner

*Primary Examiner*—Angela D. Sykes
*Assistant Examiner*—Patricia Bianco
(74) *Attorney, Agent, or Firm*—Hoffmann & Baron, LLP

(57) ABSTRACT

An implantable bypass device establishes a bypass between an artery and a vein. The device includes an implantable venous connection graft in fluid communication along a vein. The connection graft includes an elongate tubular body, an elongate access lumen extending from an intermediate location of the tubular body. An elongate tubular bypass graft has end secured in fluid communication with an artery and the other end securable to a distal end of the access lumen for establishing fluid communication between the artery and the vein through the venous connection graft. The device provides enhanced life expectancy as well desirable visualization of arterial and venous flows through the device.

20 Claims, 2 Drawing Sheets

IMPLANTABLE BYPASS DEVICE

FIELD OF THE INVENTION

The present invention relates generally to an intraluminal bypass device. More particularly, the present invention relates to an implantable bypass graft device for luminal vessels, more specifically for establishing an artery to vein bypass.

BACKGROUND OF THE INVENTION

Implantable bypass grafts are well known for reestablishing blood flow so as to avoid damaged, diseased or constricted blood vessels. One particular situation where bypass grafts are employed is to establish an artery to vein bypass. Such a bypass is established by the use of an elongate tubular bypass graft typically formed of PTFE. In certain instances, the bypass is established in a first procedure by attaching one end of the graft to the side of the brachial artery. The brachial vein is then cut in half. The inflow side of the brachial vein is sewn off and occluded. The outflow side of the brachial vein is connected end-to-end with the bypass graft.

One advantage of this first procedure employing occlusion of the brachial vein is that the bypass graft has a desirable life expectancy. One significant drawback, however, with this first procedure is that after the bypass is established a physician cannot easily distinguish between arterial and venous flows. A contrast injection is typically used by a physician to visually differentiate between arterial and venous flows. Because this first procedure occludes the venous return or inflow side of the brachial vein, both the venous and arterial sides of the bypass simultaneously fill with the contrast injection. Thus, it appears to the physician that the brachial vein has arterial flow and not venous flow, and a physician cannot properly characterize the relative amounts of arterial and venous flows.

A more common, second procedure is to attach one end of the graft to the side of the brachial artery. The graft is then formed into a U-shaped loop, the other end of the graft is then attached to the side of the brachial vein. In this second procedure the physician can more readily visualize the site because the venous flow after the bypass is a combination of arterial flow, which is rich in contrast injection, and venous flow, which is deficient in contrast injection. A physician can, thus, characterize the relative nature of arterial and venous flows with the use of this second procedure.

A disadvantage, however, of this second procedure is reduced life expectancy of the bypass graft as compared to the first procedure. In the second procedure the graft typically occludes in a quicker fashion, as compared to the first procedure, because of increased tissue response of the brachial vein at a location proximal to the bypass graft. Increased tissue response typically results at venous regions that are subject to significant contact with arterial blood flow because arterial blood has greater nutrient content as compared to venous blood.

The increased flow to the venous side brought on by the bypass graft causes an increase tissue response. The increase in tissue buildup may result in undesirable occlusion. In the first procedure where the bypass graft is connected end-to-end, the occlusion caused by tissue buildup is not significantly seen. This is believed to be due to the fact that the flow from the arterial side does not come in direct transverse contact against the venous wall because the flow is directed towards the center of the venous vessel. Where the graft and the vessel are connected end-to-end, a high rate of flow is maintained and an increased tissue response is not seen.

As compared to the first procedure, the second procedure has greater tissue response because flow from the arterial side does come in direct transverse contact against the venous wall. Such direct transverse contact is a consequence of a lack of an end-to-end connection between the graft and the vein and the increased pressure at the graft. Increased pressure is results because the blood pressure on the arterial side is significantly higher than that on the venous side.

Where occlusion does occur within a bypass graft, reintervention in the form of a balloon angioplasty can be employed until such time as the graft fully occludes. At that stage the graft will be relocated to another vein/artery.

It is therefore desirable to provide a bypass graft which may be implanted by the physician with full visualization but once implanted will not result in a significant increase in tissue response which may allude to vessel occlusion.

SUMMARY OF THE INVENTION

It is an object of the present invention to provide an intraluminal bypass device for establishing an artery to vein bypass.

It is a further object of the present invention to provide an artery to vein bypass graft which reduces the instances of tissue buildup at the site.

It is a further object of the present invention to provide an artery to vein bypass which facilitates implantation by the surgeon allowing visualization during a procedure.

In the efficient attainment of these and other objects, the present invention provides an implantable intraluminal bypass device. The bypass device establishes an artery to vein bypass. The device includes an implantable venous connection graft for securement in fluid communication along the vein. The venous connection graft has an elongate tubular body and an elongate access lumen extending from an intermediate location. An elongate tubular bypass graft has one end securable in fluid communication with the artery and the other end securable to the distal end of the access lumen. The tubular bypass graft establishes fluid communication between the artery and vein through the venous connection graft.

As shown by way of the preferred embodiment herein, the implantable bypass device may be a semi-rigid tube formed of polytetrafluoroethylene. The venous connection graft may include a textile cuff at each end for facilitating securement of the venous graft to the vein. The access lumen of the venous connection graft may extend from the tubular body at an acute angle to facilitate blood flow. The bypass graft is conformed into a generally U-shaped configuration for establishing connection between the artery and vein.

BRIEF DESCRIPTION OF THE DRAWINGS

The present invention can be further understood with reference to the following description in conjunction with the appended drawings. In the drawings.

DETAILED DESCRIPTION OF THE PREFERRED EMBODIMENT

The present invention provides an intraluminal bypass device for establishing an artery to vein bypass. The present invention avoids the disadvantages of the prior art by providing both (1) a desirable life expectancy and (2) a desirable visualization of arterial and venous flows. The present invention is a bypass with a feature of desirable life expectancy because of reduced instances of tissue buildup with the present invention, as compared to the prior art. The configuration, materials and construction of the present invention provide the bypass with, among other benefits, reduced instances of tissue buildup as the venous tissue is not placed in direct contact with significant arterial flow. Furthermore, the present invention provides for desirable visualization as its configuration permits mixing of arterial and venous flows. Such features of the present invention will be described further herein.

Figure 1:
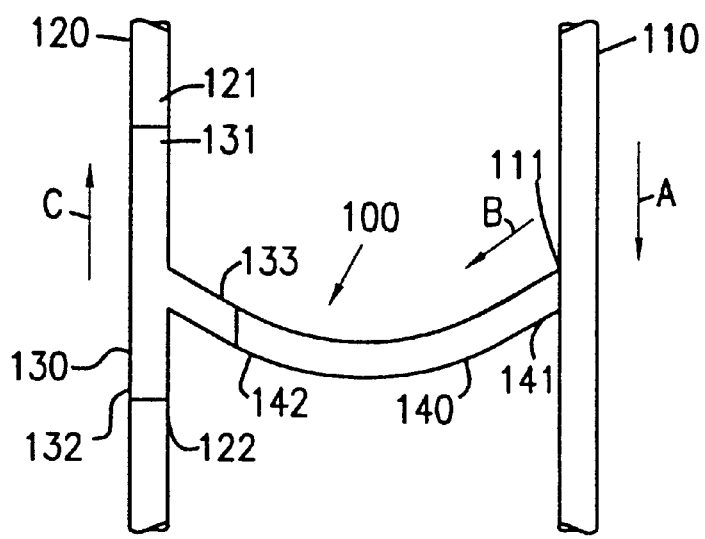
FIG. 1 is an illustration of a venous connection graft and a tubular bypass graft of the present invention for establishing an artery to vein bypass.

FIG. 1 depicts an intraluminal bypass device 100 of the present invention. Intraluminal bypass device 100 may be implanted to establish a bypass from artery 110 to vein 120. Arterial flow, which is shown in a downwardly direction as indicated by vector A in FIG. 1, is partially diverted, as indicated by vector B, through the intraluminal bypass device 100. The partially diverted arterial flow is combined with venous flow, which is in an upwardly direction as indicated by vector C in FIG. 1. Because the present invention diverts some arterial flow away from an artery to a vein, the present invention is used to establish an artery to vein bypass. Furthermore, because vein 120 is not occluded, desirable visualization is achieved with the present invention.

As depicted in FIG. 1, the intraluminal bypass device 100 includes a venous connection graft 130 and a tubular bypass graft 140. One end 141 of the tubular bypass graft 140 is securably attached, typically through suturing techniques, in fluid communication with artery 110 at lateral attachment location 111. Typically end 141 of the tubular bypass graft 140 is laterally attached to artery 110 to allow arterial flow through both the tubular bypass graft 140 and portions of artery 110 both before and after of such attachment location 111. The other end 142 of the tubular bypass graft 140 is securably attached to lateral end 133 of the venous connection graft 130 by techniques as over-molding, suturing and bonding.

The venous connection graft 130 is secured in fluid communication between two ends of vein 120 to permit venous flow through intraluminal device 100. Outflow end 121 of vein 120 is connected end-to-end to the exit end 131 of the venous connection graft 130. Similarly, inflow end 122 of vein 120 is connected end-to-end to the entrance end 132 of the venous connection graft 130. Arterial flow from artery 110 via tubular bypass graft 140 is combined with venous flow from vein 120 to establish the artery to vein bypass. Venous connection graft 130 is further described hereinbelow in conjunction with FIG. 2.

Tubular bypass graft 140 is a semi-rigid tube formed from biocompatible material or from biological material, such as a portion of a saphenous vein. Preferably, tubular bypass graft 140 is formed from polytetrafluoroethylene (PTFE) or a synthetic polyester fiber, such as Dacron. As used herein, the term of "semi-rigid" refers to both a degree of rigidity necessary for the present invention to sustain arterial pressures without failure thereof and a degree of flexibility necessary for the present invention to absorb, to some degree, the effects of increased arterial pressure, to deform with bodily movement to prevent damage to bodily tissues or vessels and to prevent the present: invention from protruding from under the skin.

As depicted in FIG. 1, tubular bypass graft 140 is secured between artery 110 and the venous connection graft 130 in a curved or U-shaped fashion. The U-shape provides flexibility to the intraluminal bypass device 100. Such flexibility facilitates insertion by a surgeon. Furthermore, the U-shape effects, to some degree, the nature of arterial flow as the arterial flow enters the venous connection graft 130. Such effects will also be described in further detail below in conjunction with FIG. 2.

Figure 2:
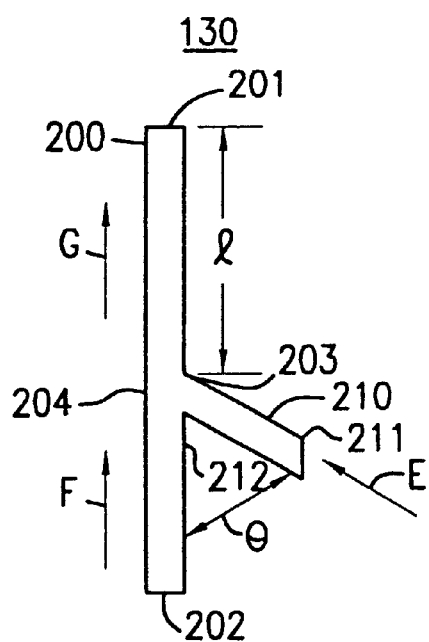
FIG. 2 is a view of the venous connection graft of FIG. 1.

As depicted in FIG. 2, venous connection graft 130 includes tubular body 200 and access lumen 210 in fluid communication therewith. Both tubular body 200 and access lumen 210 are elongated tubular structures. Access lumen 210 extends from tubular body 200 at an intermediate location 203 at an angle, θ. The angle θ is preferably less than 90 degrees to reduce turbulence as arterial flow from access lumen 210 enters the tubular body 200.

Arterial flow, as indicated by vector E, enters end 211 of access lumen 210. The arterial flow then exits end 212 of access lumen 210 and enters into tubular body 200. The arterial flow may come in direct transverse contact against an interior wall portion 204 of tubular body 200 adjacent intermediate location 203. At location 203 proximate the exit end 212 of lumen 210, the arterial flow is combined with venous flow, which is indicated by vector F. At this location within tubular body 200 the arterial flow and the combined arterial/venous flow may be characterized as unsteady laminar flow or turbulent flow. As used herein, the term "turbulent flow" refers to a motion of a fluid having local velocities and pressures that fluctuate randomly.

As the tubular body 200 extends beyond the location where arterial and venous flows are combined, the turbulent flow or unsteady laminar flow is transformed to laminar flow before the arterial/venous flow, which is indicated by vector G, exits tubular body 200 and comes in contact with venous tissue. As used herein, the term "laminar flow" refers to nonturbulent flow. Such laminar flow is further characterized as smooth and regular motion where the direction of motion at any point remains substantially constant as if the fluid were moving in a series of layers of different velocity sliding over one another without mixing.

The length, l, of tubular body 200 between the access lumen 210 and the exit end 221 of tubular body 200 is set to ensure that the combined arterial and venous flow at the exit end 221 is substantially laminar flow. The length l depends in part upon the angle θ. Smaller values of θ typically result in decreased turbulent flow at the location where arterial and venous flows are combined. Such decreased turbulent flow reduces the requirement of the length l. Such proportionality between l and θ influences the configuration of venous connection graft 130. It will be clear to those skilled in the art how to vary l and θ to obtain the desired laminar flow.

Referring again to FIG. 1, as the outflow end 121 of vein 120 and the exit end 131 of venous connection graft 130 are connected end-to-end, laminar flow is maintained as the combined arterial and venous flow exits the venous connection graft 130 and enters vein 120. With laminar flow, higher regions of flow are maintained near the center of vein 120 as compared to locations near the venous wall. Such laminar flow, along with the feature of reduced direct transverse contact of arterial flow with venous walls, reduces tissue response at the venous walls and increases life expectancy of the bypass device. The desired life expectancy of the bypass device is achieved even with experiencing higher fluid pressures due from arterial flow, as compared to venous flow.

In the preferred embodiment venous connection graft 130 is a semi-rigid, tubular structure formed from biocompatible material. Preferably, venous connection graft 130 is formed from a suitable PTFE or a synthetic polyester fiber, such as Dacron. Similarly, venous connection graft 130 is preferably constructed of injection molded PTFE or Dacron polyester. Although other construction techniques may be used with the present invention, such injection molding typically results in smoother interior surfaces as compared to devices constructed by other techniques, such as extrusion techniques. Such smoother surfaces reduce the length l requirements of the tubular body 200.

Tubular body 200 and access lumen 210 may be separately fabricated by the above-described techniques and then securely affixed to one and the other in fluid communication to form the venous connection graft 130. Techniques, such as bonding, over-molding and suturing, may suitably be used to so affix tubular body 200 and access lumen 210. In the preferred embodiment, venous connection graft 130 may be fabricated in one-piece without the need for subsequently affixing tubular body 200 and access lumen 210.

Figure 3:
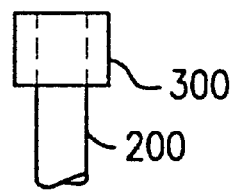
FIG. 3 is a view of a textile cuff attached to an end of the venous graft connection.

The present invention further provides for the end-to-end connection of the vein 120 to the ends 201 and 202 of tubular body 200. As depicted in FIG. 3, a material cuff 300 may be located at each of the two ends of tubular body 200 and is securable fixed thereon. Such material cuff 300 could be constructed from a piece of biocompatible material, such as PTFE or Dacron polyester. Material cuff 300 may be preferably formed into a textile or a mesh shape to promote bonding of venous tissue thereon. While materials cuffs may be employed, the present invention also completes other securement means to facilitate such end-to-end connections.

Figure 4:
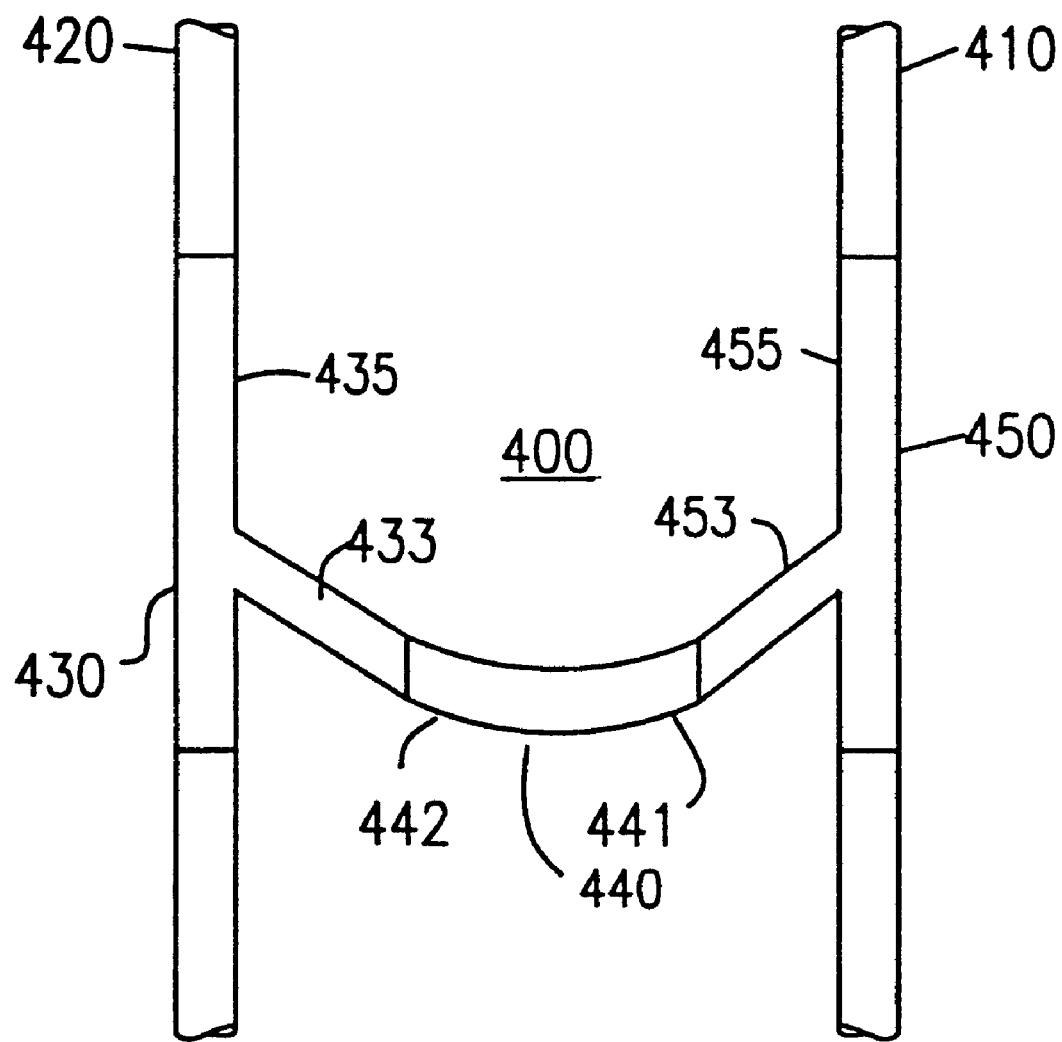
FIG. 4 is an illustration of a further embodiment of the present invention having a venous connection graft and an arterial connection graft.

Furthermore, the present invention is not limited to the use of a single connection graft. As depicted in FIG. 4, intraluminal bypass device 400 includes a venous connection graft 430, an arterial connection graft 450 and a tubular bypass graft 440, interrelated as shown, for establishing a bypass between artery 410 and vein 420. Tubular bodies 435 and 455 of respective connection grafts 430 and 450 are securably implantable in fluid communication within vein 420 and artery 410, respectively. The venous connection graft 430 and the arterial connection graft 450 are similar to the above described venous connection graft 130.

The tubular bypass graft 440 is also similar to the above described tubular bypass graft 140. One end 441 of tubular bypass graft 440 is securable attached in fluid communication to access lumen 453 and the other end 442 of tubular bypass graft 440 is securable attached in fluid communication to access lumen 433. In the embodiment shown in FIG. 4, fluid communication is established between artery 410 and vein 420 through bypass devices 440 and 450, thereby preventing blood contacts with the vessel at the location of turbulent flow.

The preferred embodiment of the present invention describes bypass device 100 for use as an artery to vein bypass. However, the bypass device of the present invention may suitably be used to establish other luminal bypasses, such as an artery to artery bypass or a vein to vein bypass. These other luminal bypasses may contain one connection graft, as depicted in FIG. 1, or may contain two connection grafts, as depicted in FIG. 4. For example, blood vessels 410 and 420 may be an artery and a vein as depicted in FIG. 4, may both be veins, or may both be arteries.

Various changes to the foregoing described and shown structures would now be evident to those skilled in the art. Accordingly, the particularly disclosed scope of the invention is set forth in the following claims.

What is claimed is:

1. An implantable intraluminal bypass device for establishing a blood vessel to blood vessel bypass comprising:

a one-piece integrally molded connection graft for securement, in fluid communication, along a first blood vessel without occlusion of said first blood vessel said connection graft having an elongate tubular body and elongate access lumen extending from an intermediate location of said tubular body; and an elongate tubular bypass graft having one end securable in fluid communication with a second blood vessel without occlusion of said second blood vessel and the other end securable to a distal end of said access lumen for establishing fluid communication between said second blood vessel and said first blood vessel through said connection graft;

wherein said elongate access lumen angularly extends from said intermediate location to provide the fluid communication in laminar flow without direct traverse contact of the fluid communication with inner walls of said first and said second blood vessels.

2. A device of claim 1 wherein said connection graft is formed of biocompatable material.

3. A device of claim 2 wherein said biocompatable material is polytetrafluoroethylene.

4. A device of claim 2 wherein said biocompatable material is a synthetic polyester fiber.

5. A device of claim 2 wherein said connection graft is injection molded.

6. A device of claim 2 wherein said connection graft is semi-rigid.

7. A device of claim 1 wherein said connection graft further includes a securement means at each end of said elongate tubular body for facilitating said securement of said ends to said first blood vessel.

8. A device of claim 7 wherein said securement means includes a textile cuff.

9. A device of claim 1 wherein said access lumen extends from said tubular body at an angle less than 90°.

10. A device of claim 9 wherein said tubular body has an exit end for discharging fluid into said first blood vessel and further wherein a length of said tubular body from said intermediate location to said exit end is defined to provide laminar flow of the discharging fluid into said first blood vessel.

11. A device of claim 9 wherein said tubular bypass graft is curved.

12. A device of claim 1 wherein said connection graft is securable to a vein.

13. A device of claim 1 wherein said connection graft is securable to an artery.

14. A device of claim 1 further comprising a second connection graft along said second blood vessel, said second connection graft having a second elongate tubular body and a second elongate access lumen extending from an intermediate location of said second access lumen.

15. A method of establishing a blood vessel to blood vessel bypass comprising the steps of:

implanting a one-piece integrally molded elongate tubular connection graft in fluid communication within a first blood vessel, said connection graft having an access lumen extending from an intermediate location thereof;

attaching one end of an elongate tubular bypass graft to a second blood vessel so as to maintain flow through said second blood vessel; and attaching the other end of said bypass graft to said access lumen for establishing flow to said connection graft;

wherein the flow from said second blood vessel does not come in direct traverse contact with an inner wall of said first blood vessel and further wherein the flow from said second blood vessel is laminar flow.

16. A method of claim 15 wherein said connection graft includes textile cuffs at each end thereof and wherein said implanting step includes suturing said textile cuffs to said first blood vessel.

17. A method of claim 15 further including the step of:
forming said bypass graft into a curved configuration.

18. A method of claim 15 wherein said connection graft is implantable within a vein.

19. A method of claim 15 wherein said connection graft is implantable within an artery.

20. A method of claim 15 further including the step of implanting a second elongate tubular connection graft in fluid communication within said second blood vessel, said second connection graft having a second access lumen from an intermediate location thereof, wherein said one end of said bypass graft is attached to said second access lumen.

* * * * *